United States Patent
Johnson et al.

[11] Patent Number: 5,858,020
[45] Date of Patent: Jan. 12, 1999

[54] MODULAR PROSTHESIS

[75] Inventors: Wesley D. Johnson, Chanhassen; Richard C. Emery, White Bear Lake, both of Minn.

[73] Assignee: Metagen, LLC, Menomonie, Wis.

[21] Appl. No.: 567,650

[22] Filed: Dec. 5, 1995

[51] Int. Cl.$^6$ .................................. A61F 2/36; A61F 2/30
[52] U.S. Cl. .................................. 623/23; 623/18; 606/78
[58] Field of Search .................. 606/78, 62; 623/18, 623/22, 23, 19

[56] References Cited

U.S. PATENT DOCUMENTS

| | | |
|---|---|---|
| 3,981,307 | 9/1976 | Borysko .................................. 606/78 X |
| 4,170,794 | 10/1979 | Zeibig et al. . |
| 4,170,990 | 10/1979 | Baumgart et al. .......................... 606/78 |
| 4,520,511 | 6/1985 | Gianezio et al. . |
| 4,693,724 | 9/1987 | Rhenter et al. . |
| 4,756,711 | 7/1988 | Maï et al. .................................. 623/23 |
| 4,896,955 | 1/1990 | Zider et al. .................................. 351/41 |
| 4,921,499 | 5/1990 | Hoffman et al. ............................ 623/16 |
| 4,938,773 | 7/1990 | Strand . |
| 4,995,883 | 2/1991 | Demane et al. . |
| 5,002,578 | 3/1991 | Luman . |
| 5,013,507 | 5/1991 | Julien et al. .............................. 264/219 |
| 5,035,712 | 7/1991 | Hoffman .................................. 623/16 |
| 5,080,685 | 1/1992 | Bolesky et al. . |
| 5,120,175 | 6/1992 | Arbegast et al. ........................ 411/501 |
| 5,190,546 | 3/1993 | Jervis . |
| 5,397,360 | 3/1995 | Cohen . |
| 5,415,660 | 5/1995 | Campbell et al. .......................... 606/62 |
| 5,507,826 | 4/1996 | Besselink et al. . |
| 5,584,695 | 12/1996 | Lal Sachdeva et al. ................. 433/173 |

FOREIGN PATENT DOCUMENTS

| | | |
|---|---|---|
| 0 311 208 | 4/1989 | European Pat. Off. . |
| 0 610 575 | 8/1994 | European Pat. Off. . |
| 0 634 154 | 1/1995 | European Pat. Off. . |
| 2651119 | 3/1991 | France . |
| 2 722 679 | 1/1996 | France . |
| 3838388 A | 5/1990 | Germany .................................. 623/23 |
| 3159-645-A | 7/1991 | Japan .................................. 623/23 |
| 405003885 | 1/1993 | Japan .................................. 433/174 |
| 406000198 | 1/1994 | Japan . |
| 1110447 A | 8/1984 | U.S.S.R. .................................. 606/78 |
| 1351591 | 11/1987 | U.S.S.R. .................................. 606/78 |
| 1548964 | 7/1979 | United Kingdom . |
| 92 14423 | 9/1992 | WIPO . |
| WO 95 13757 | 5/1995 | WIPO . |

Primary Examiner—David H. Willse
Attorney, Agent, or Firm—Fredrickson & Byron, PA

[57] ABSTRACT

A kit for producing a modular prosthesis is provided, the kit including a first prosthesis member having a cavity such as a bore formed in it, and a clamp releasably clamped in the cavity. The clamp, which may be a rod having an axial bore through a portion of its length, is subjected to an external stimulus such as a stretching force to cause the diameter of the clamp to be reduced enough so that the clamp is received in the cavity. As the stimulus is withdrawn, the clamp returns toward its initial configuration, and in so doing, expands against the walls of the cavity. A second prosthesis member may be configured to receive a portion of the first member such that expansion of the clamp in the cavity of the first member concurrently causes that member to expand into contact with the second member to clamp the members together.

20 Claims, 6 Drawing Sheets

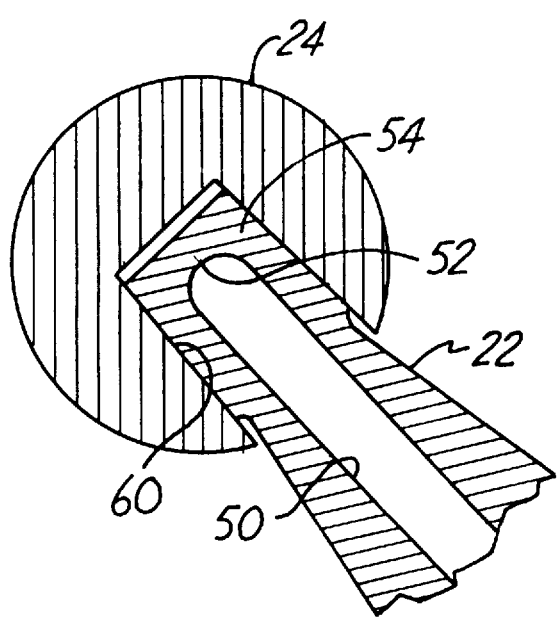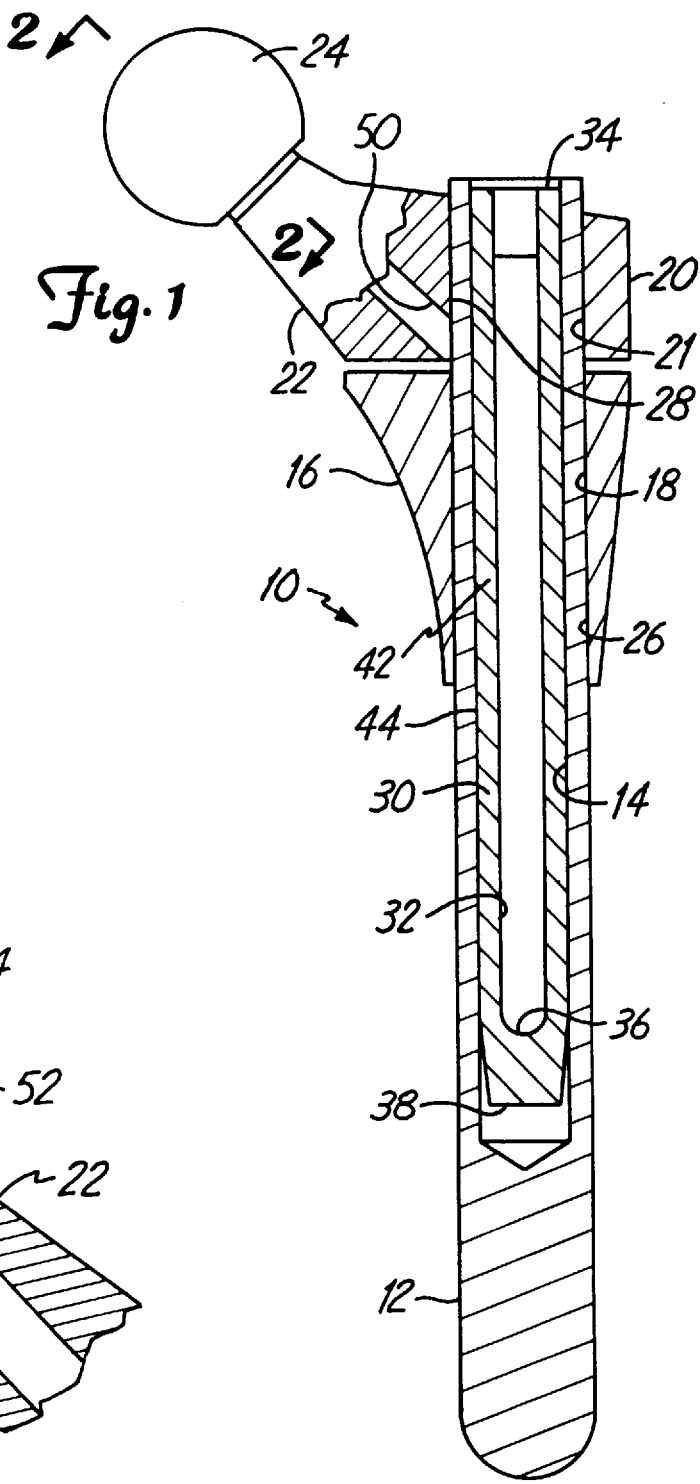

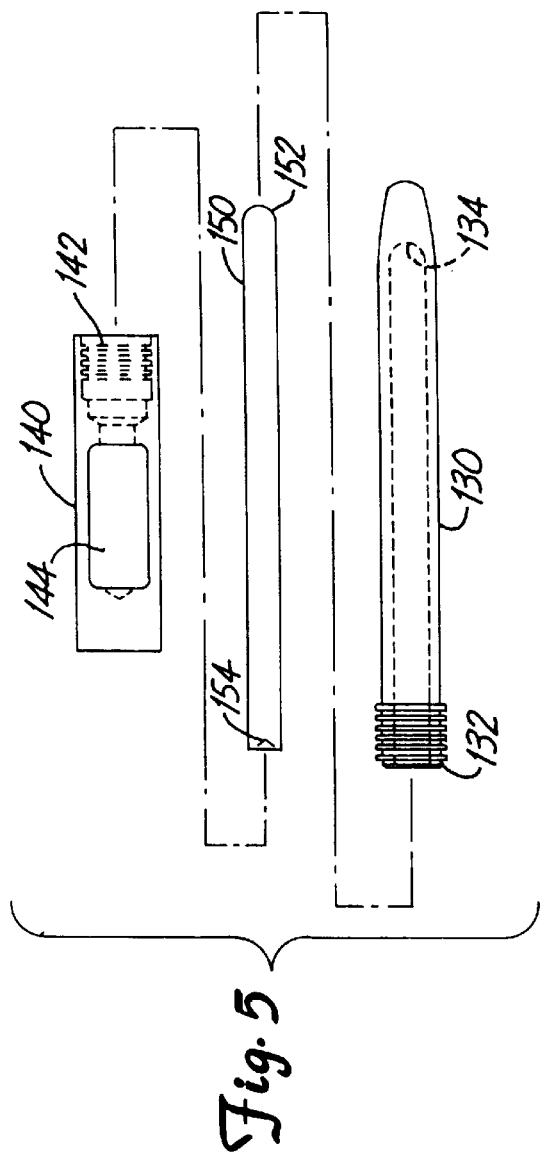
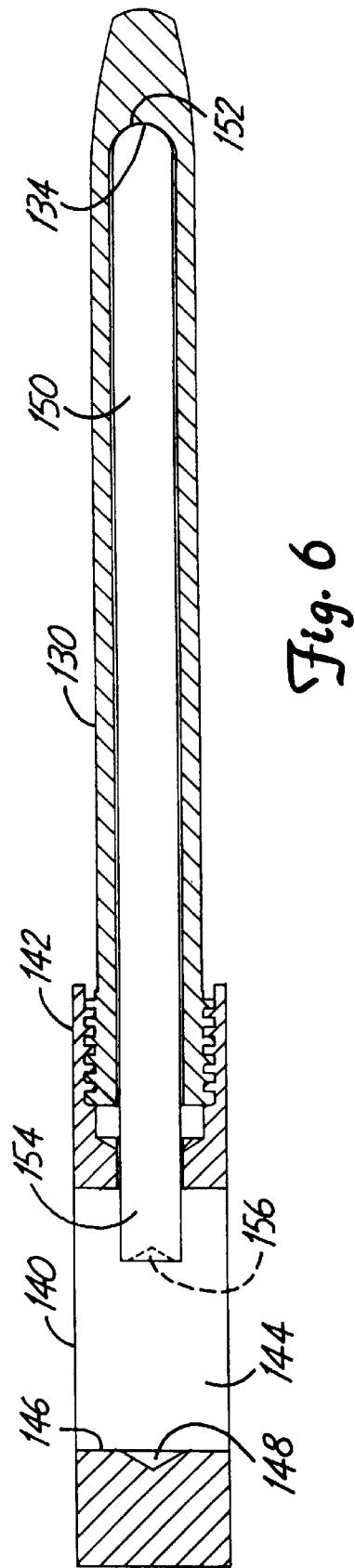

MODULAR PROSTHESIS

FIELD OF THE INVENTION

This invention relates to the field of medical prostheses and particularly to prostheses for use as replacements for diseased or damaged joints.

BACKGROUND OF THE INVENTION

Prostheses for replacement of joints commonly involve two parts having mutually articulating surfaces, and structure for mounting the parts to bone. To duplicate closely the structure and function of natural joints, the prostheses parts must be carefully shaped and sized, and must be properly oriented by the surgeon with respect to each other and with respect to the anatomy of the patient.

To achieve good surgical results, a surgeon should have as much freedom as possible during the surgical implantation procedure to vary the shape, size and orientation of prosthesis parts. Mainly for this reason, efforts have been made to provide prostheses that are modular in form so that various elements of a prosthesis can be individually selected and the prosthesis can be assembled and oriented according to the anatomical needs of the patient.

Modular prostheses for the hip joint are shown, for example, in Boleski et al., U.S. Pat No. 5,080,685, Gianezio et al., U.S. Pat. No. 4,520,511, Demane et al., U.S. Pat. No. 4,995,883, Luman, U.S. Pat. No. 5,002,578 and Rhenter et al., U.S. Pat. No. 4,693,724. Such prostheses for the most part involve a substantial number of parts that are held together in one configuration or another by means of mounting screws which operate to draw together tapered connections of the parts. Although some freedom of selection is provided by previous modular prostheses, the use of threaded mounting screws and tapered connections can lead to loosening of the parts and to other problems. Physical and chemical corrosion can become substantial problems due to weakening of the prosthesis and to biologic responses to corrosion debris and byproducts. See Jacobs, J. J. et al., *Biological Activity of Particulate Chromium-Phosphate Corrosion Products,* Collected Papers of the 21st Annual Meeting of the Society for Biomaterials, Mar. 18–22, 1995, p. 398, and Urban, Robert M., et al., *Corrosion Products From Modular-Head Femoral Stems of Different Designs and Material Couples,* Collected Papers of the 21st Annual Meeting of the Society for Biomaterials, Mar. 18–22, 1995, p. 326. Fretting corrosion caused by relative motion between adjoining surfaces leads to the production of debris which in turn may lead to accelerated wear between normally articulating joint parts of a prosthesis and to osteolysis. When gaps occur between adjacent surfaces of prosthesis parts, oxidation of the surfaces may lead to formation of an acidic environment and hence to chemical attack of the surfaces (commonly referred to as crevice corrosion).

It would be desirable to provide a modular prosthesis kit having elements that can be freely chosen and oriented by the surgeon in the operating arena and that can be strongly and firmly fastened to one another without the need for screw fasteners or tapered connections that are drawn together.

SUMMARY OF THE INVENTION

The present invention makes use of a clamp capable of firmly clamping to a prosthesis member and that may be used to firmly clamp together selected parts of a modular prosthesis. The clamp has a "rest" configuration having a dimension in one direction that can be reduced by applying to it an external stimulus, with concurrent expansion of the clamp in a second direction normal to the first direction, so that the clamp may be received in a cavity of a prosthesis member. Upon withdrawal of the external stimulus, the clamp seeks to return toward its "rest" configuration, the clamp dimension in the one direction increasing so that the clamp presses upon the cavity walls to strongly clamp to the prosthesis member.

Thus, in one embodiment the invention relates to a modular prosthesis kit comprising a first member having walls defining a cavity, and a clamp releasably clampable within said cavity. The clamp has a first, rest configuration having a predetermined dimension in a first direction and being responsive to an external stimulus to assume a second configuration having a lesser dimension in said first direction with concurrent increase of a dimension in a second direction normal to the first direction to permit the clamp to be at least partially received in the cavity. The predetermined dimension is so chosen that upon withdrawal of the external stimulus, the clamp returns toward its rest configuration with consequent increase in its dimension in the first direction sufficient to strongly clamp to said member.

In another embodiment, the invention comprises a modular prosthesis kit that includes instrumentation for assembly, comprising a first prosthesis member having walls defining a cavity and a clamp releasably clampable within said cavity. The clamp has a first, rest configuration having a predetermined dimension in a first direction. An instrument is provided for applying a stretching force to said clamp in a second direction normal to said first direction to reduce said dimension in the first direction enough to permit said clamp to be received in said cavity. The predetermined dimension is such that upon removal of the stretching force, the clamp returns toward its rest configuration with consequent increase in its dimension in the first direction sufficient to strongly clamp to said first prosthesis member. In a preferred embodiment, the prosthesis kit includes a second member configured to snugly receive at least a portion of the first member in any of several orientations. The cavity walls of the first member are configured to expand into clamping contact with the second member as the clamp returns toward its rest configuration to fixedly support the second member in a predetermined orientation with respect to the first member.

In yet a further embodiment, the invention relates to a method for assembling members of a modular prosthesis. A first prosthesis member is provided with walls defining a cavity, and a clamp is provided having a first, rest configuration having a predetermined dimension in a first direction. The clamp is subjected to an external stimulus, preferably a physical tensioning stimulus, to reduce the dimension in the first direction with concurrent expansion of a clamp dimension in a second direction normal to the first direction to enable the clamp to be received in the cavity of the first prosthesis member. The external stimulus is thereafter withdrawn to allow the clamp to return toward its first, rest configuration with consequent increase in its dimension in the first direction sufficient to strongly clamp to said first prosthesis member.

Preferably, the clamp and the cavity of the first prosthesis member have confronting, clamping surfaces that, when clamped, are substantially congruent so as to provide surface-to-surface contact between the clamp and first member and the prosthesis is free of gaps between confronting surfaces. Similarly, if a second prosthesis member receives and becomes clamped to the first member, preferably the clamping surfaces of these members are substantially congruent so as to provide surface-to-surface contact between the clamping surfaces of the first and second members and the prosthesis is free of gaps between confronting surfaces. Such surface-to-surface contact promotes uniform loading along the clamping surfaces.

BRIEF DESCRIPTION OF THE DRAWING

FIG. 1 is a side view, in partial cross-section, of a portion of a hip joint prosthesis in accordance with the invention;

FIG. 2 is a cross-sectional, broken away view taken across line 2—2 of FIG. 1;

FIG. 5 is an exploded assembly view of parts of instrumentation for use in the assembly of the hip joint prosthesis of FIG. 4;

FIG. 6 is a view of the parts of FIG. 5 as assembled;

DETAILED DESCRIPTION OF THE PREFERRED EMBODIMENTS

Figure 3:
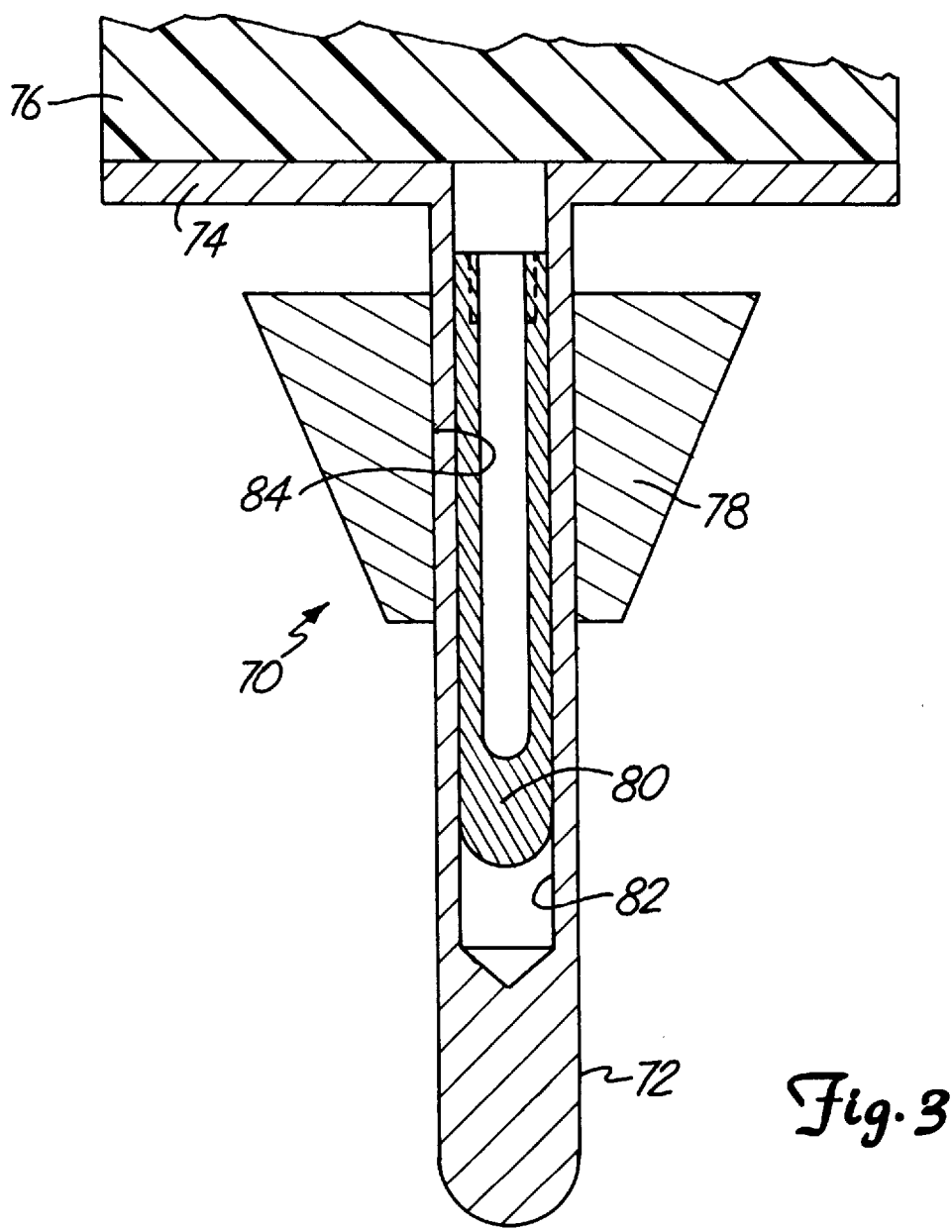
FIG. 3 is a schematic front view of the tibial portion of a knee joint in accordance with the invention.

With reference first to FIG. 1, a modular hip prosthesis is designated 10, and comprises an elongated stem 12 sized to be received in a surgically prepared intramedullary canal of the femur. Axial bore 14 is formed in the stem 12. A body member 16 is provided with a bore 18 sized to closely receive the stem 12, the body having a generally triangular shape when viewed from the side and configured to fit the surgically sculpted proximal end of the intramedullary canal of the femur. Proximally of the body 16 is positioned a neck member 20 having a bore 21 sized to closely receive the upper end of the stem 12, the neck including an angled extension 22 terminating in a ball 24 sized to articulate with an appropriately sized and shaped socket prosthesis (not shown) to be mounted in the acetabular recess of the pelvis.

A clamp 30 is shown in FIG. 1 as an elongated metal rod having an axial bore 32 that extends from its proximal end portion 34 to a floor 36 short of the distal end portion 38 of the clamp. Near its upper end, the axial bore 32 has a distally facing shoulder fashioned to receive a placement instrument, as will be described below.

The clamp 30 is shaped and sized such that at body temperature, its diameter, when not constrained in the stem 12, will be slightly larger than the diameter of the bore 14 of the stem. The diameter 21 of the neck bore and the diameter 18 of the body bore, on the other hand, are essentially the same as the outer diameter of the stem 12; that is, the stem is snugly but slidably received in the bores 18, 21 so that the body and the neck can be moved by hand upon the stem without difficulty.

The clamp 30, before installation in the bore 14 of the stem, first must be altered so that its diameter is slightly less than the bore diameter of the stem. This is accomplished by physically stretching the clamp in its long or axial direction to cause the diameter of the clamp to shrink sufficiently to enable the clamp to be inserted in the bore 14. Although the clamp may be made from various metals as described below, a preferred metal is a shape memory alloy such as nitinol, in its superelastic state in which applied stress results in a reversible martensitic phase transition. When a nitinol claimp 30 is stretched as described above, and providing that its temperature is maintained substantially above its ausenite finish temperature (the temperature at which the alloy is completely in its austenitic form), a transition from the austenite phase to the martensite phase occurs. This is known as stress induced martensite formation and is the basis for the phenomenon known as pseudoelasticity or superelasticity. The shape memory alloy will remain at least partially in the martensite phase as long as the external stress is maintained. Upon release of the stress, however, the clamp 30 will return to the austeniste phase and toward its original shape and size. Because the clamp is constrained within the dimensions of the stem bore 14, however, it will not be able to completely resume its original shape and size. As a result, the clamp 30 will exert a continuous force against the bore 14 of the stem 12.

Alternatively, the clamp may be made from a shape memory alloy such as nitinol in which the material is capable of undergoing a temperature-induced phase change. In this embodiment, the shape memory alloy is so configured that when in its stable phase at body temperature, its diameter is slightly greater than the diameter 14 of the stem. At a lower temperature, however, the clamp may be deformed into a different physical shape in which it is slightly longer and slightly more slender than in its stable form at body temperature, this configuration permitting the clamp to slide into the bore 14 of the stem. In this embodiment, once the shape memory alloy is warmed and passes through its phase transition temperature range, it expands toward its stable configuration at body temperature, thereby pressing outwardly with a continuous force upon the bore of the stem.

Thus, both when using a temperature-induced phase change for a shape memory alloy, and when using a physical lengthening of the clamp, the clamp tends to return to a configuration which may be referred to as a "rest" configuration at body temperature. The rest configuration, however, has a transverse dimension (the diameter in the case of a rod having a circular cross-section) that is slightly larger than the transverse dimension of the stem bore, and as a result the clamp pushes outwardly strongly upon the stem bore and becomes firmly clamped in the stem bore.

As shown in FIG. 1, the walls 42 of the clamp have outer surfaces 44 that engage and push outwardly upon the bore 14. When appropriately in place, the outer wall 44 of the clamp pushes outwardly upon the surface of the stem bore 14, and the walls of the stem, in turn, are forced outwardly into contact with the inner surface 26 of the body 16 and also with the inner surface 28 of the neck 20.

Preferably, the outer surface of the clamp 30 is generally cylindrical and makes substantial surface-to-surface contact with the surface of the bore 14. Moreover, the stem wall is sufficiently flexible as to enable the outer wall of the stem to expand into contact with the bores of both the body and the shoulder, even when these bores are slightly different in diameter. A feature of a preferred embodiment of the invention is that the clamped surfaces—that is, the confronting surfaces of the clamp and first member, and the confronting surfaces of the first and second members—mate in surface-to-surface contact to fairly uniformly distribute the compressive forces over the clamped surfaces and preferably to avoid gaps between confronting surfaces. As used herein, a "gap" is the thin void space formed between slightly spaced confronting surfaces of a prosthesis when assembled, as, for example, the space formed between an elongated, smoothwalled rod having threads at one end and the bore receiving the rod. If the clamp is a cylinder having a circular cross-section and the cavity is a circular bore, the compressive clamping force exerted by the clamp against the walls of the bore would be primarily radial and substantially uniform along the length of the clamp. One may vary as desired the concentration of compressive forces between the clamp (and between prosthesis members) by varying the shapes of the clamping surfaces. For example, if the cross-sections of the clamp and recess were oval rather than circular, one would expect the compressive clamping force to be somewhat greater in the longer transverse dimension than in the shorter transverse dimension.

The invention in another embodiment is shown in FIG. 2, in which the ball 24 is firmly mounted to the angled neck extension 22. The ball 24 and the neck member 20 (from which extends the angled extension 22) generally will be assembled as a subunit, and the subunit will then be assembled with the body and stem as mentioned above.

As shown in FIG. 2, the angled extension 22 has an internal bore 50 that is open at one end and is closed at its other end 52. The bore 50 extends downwardly and laterally as shown in FIGS. 1 and 2, and opens into the bore 28. The distal end of the angled neck has a tapered head 54 that is received within a tapered bore 60 formed in the ball 24. In this embodiment, the angled neck 22 functions not only as a part of the prosthesis but also as the clamp. To positively and firmly connect the ball 24 to the angled neck, one first elongates the angled neck in the manner described above in connection with the clamp 30. Upon elongation of the angled neck 22 sufficient to enable the head 54 to be snugly received in the ball, the stretching force imparted by the instrument is withdrawn, and the neck 22 returns toward its original, "rest" configuration, the outer wall of the head 54 bearing outwardly against the confining walls of the bore 60 to firmly clamp the ball to the angled neck. Referring to FIG. 1, it will be noted that the bore 50 is fully accessible through its open end prior to mounting of the neck 20 upon the stem 12. It may also be noted that the clamp and the cavity, although circular in cross-section and making mutual surface-to-surface contact, are tapered rather than cylindrical, illustrating how the shape of the clamp and cavity may be varied.

With reference to FIG. 3, a tibial tray component is shown generally as 70 and comprises a stem 72 adapted to be received in the surgically prepared intramedullary canal of the tibia in a known fashion. The stem terminates upwardly in a metal tray 74 which in turn supports a bearing insert 76 of high molecular weight polyethylene or the like. The latter is adapted to articulate with the condyles at the distal end of the femur, or with the condyles of a prosthetic femoral implant, all in a known fashion. Near the upper end of the stem is positioned a shoulder 78 which fits in the surgically prepared upper end of the tibial intramedullary canal, and serves to support the upper end of the stem.

A clamp such as that described above is shown at 80 in FIG. 3. It is desirably cylindrical in cross section, having a diameter at body temperature that is slightly greater than the diameter of a bore 82 formed axial within the stem 72. The clamp 80 may be inserted by the same method described in connection with the clamp 30 of FIG. 1. When the stretching force is withdrawn, the clamp returns toward its "rest" configuration and its walls press outwardly against the walls of the stem 72, causing the latter in turn to clamp strongly to the walls of the bore 84 of the shoulder member 78.

Figure 4:
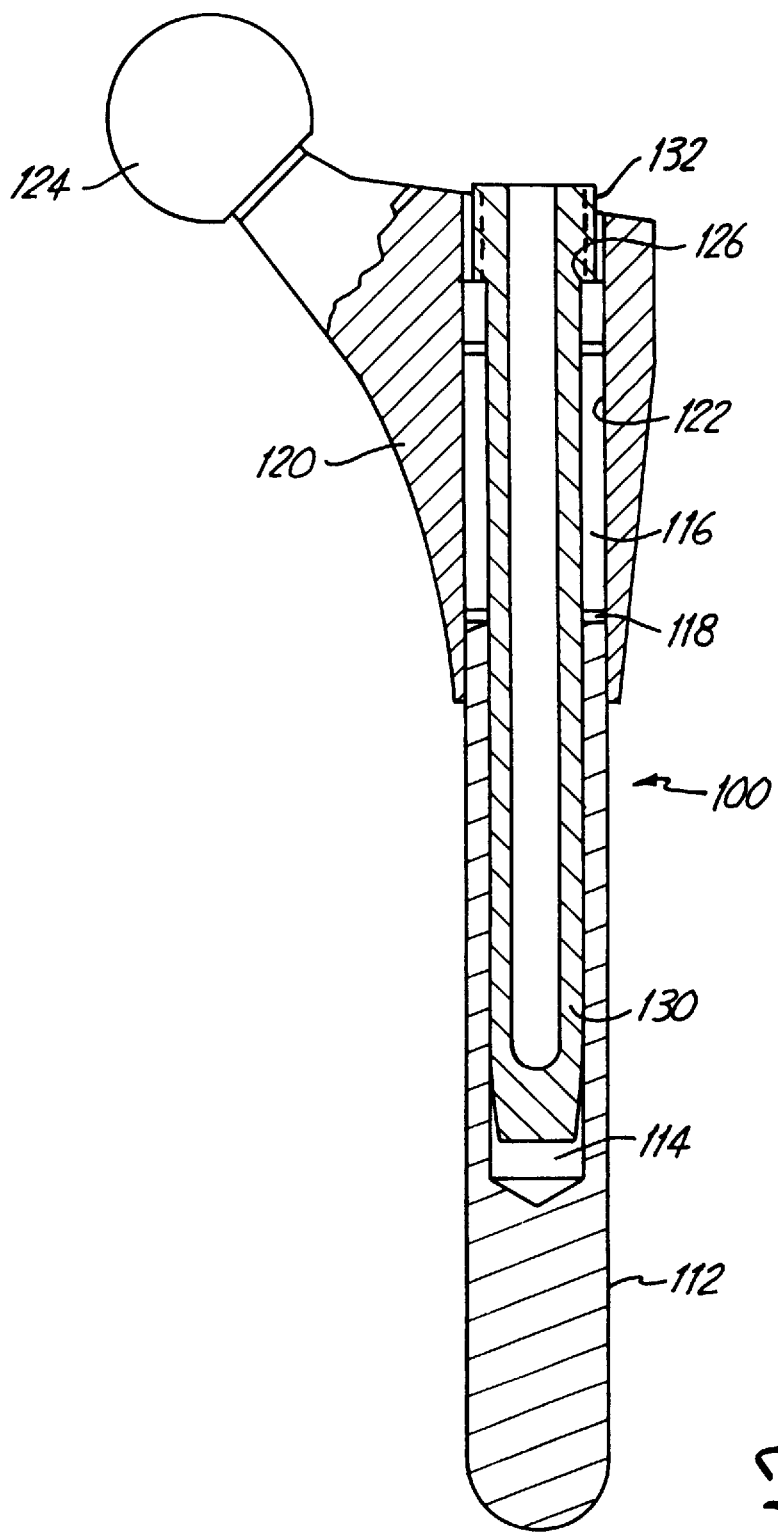
FIG. 4 is a side view, in partial cross-section, of a portion of another hip joint prosthesis similar to that of FIG. 1.

A slightly modified hip joint prosthesis is depicted in FIG. 4 as 100, the prosthesis having a stem 112 adapted for insertion in the intramedullary canal of the femur. An axial bore 114 is formed in the stem, and the walls of the stem near its proximal end may have longitudinal slots 116 formed therein, the slots ending in round holes 118 to avoid stress concentration areas. The slots 116 enable the wall of the stem to expand more easily, and are spaced evenly about the circumference of the stem. Four slots may be employed. A body 120 is provided with an internal bore 122 sized to snugly receive the stem, the body bearing a ball 124 similar to ball 24 of FIG. 1. The upper or proximal end of the body 120 extends slightly beyond the proximal end 126 of the stem.

Within the stem is received a hollow, tubular clamp 130 similar to the clamp 30 shown in FIG. 1. Clamp 130 has a proximal, externally threaded end portion 132 that extends beyond the proximal end 126 of the stem but is yet preferably retained in the proximal end portion of the body bore 122, all as shown in FIG. 4.

Figure 7:
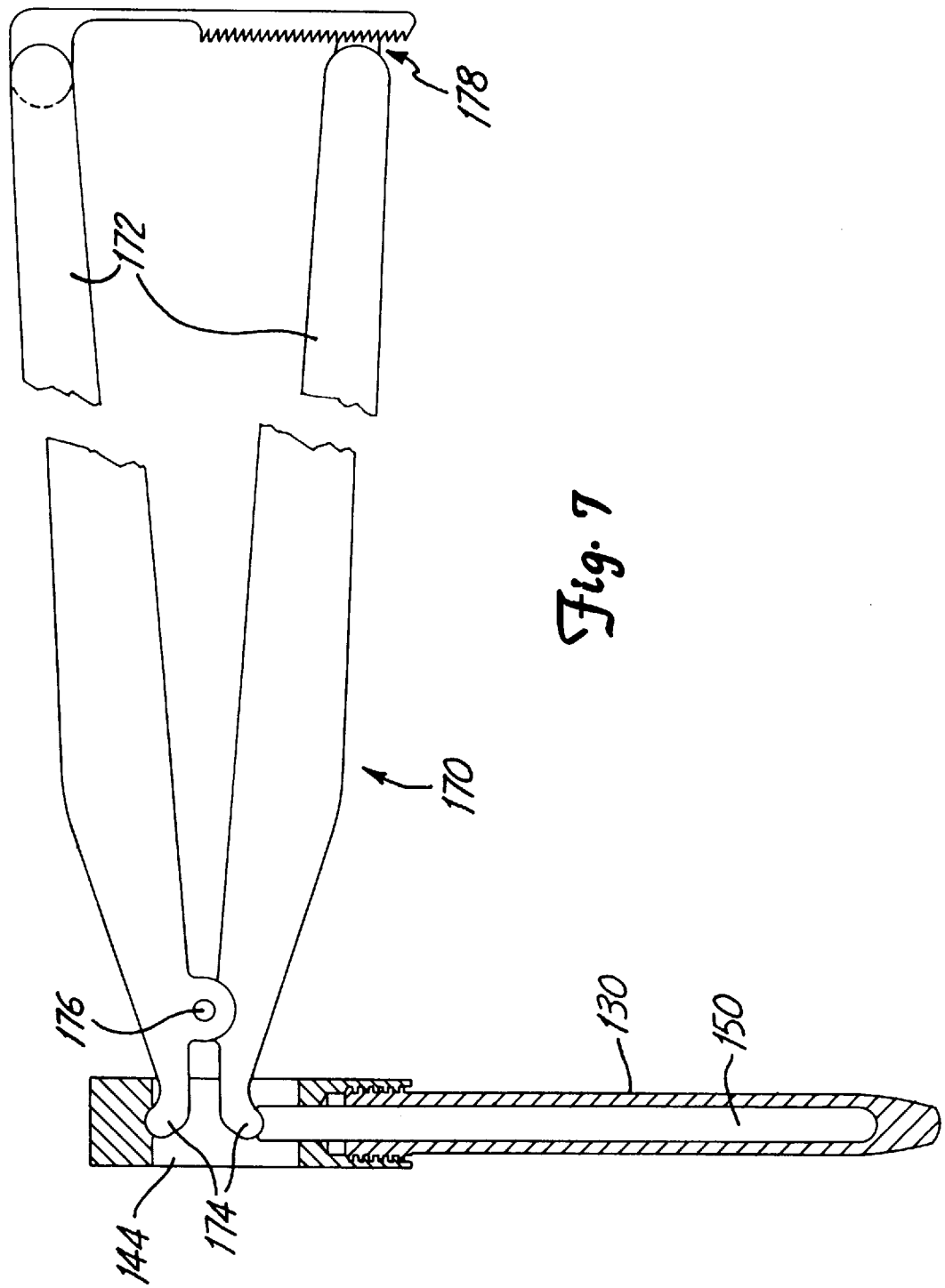
FIG. 7 is a view of the assembly of FIG. 6 together with a manually operated force generating device.

FIGS. 5–7 depict instrumentation for applying tensile stress to the clamp typified as 130 in the drawing. Shown at 140 is a tubular gripping tool having an open distal end portion 142 that is internally threaded to receive the external threads of the proximal end portion 132 of the clamp. Square threads preferably are used. An aperture 144 is formed in the gripping tool 140 proximal of its distal end portion 142. An elongated pushing rod 150 is received in the hollow clamp, and has a distal end 152 shaped to engage the confronting distal end wall 134 of the clamp in surface-to-surface contact. The proximal end 154 of the pushing rod is accessible through the aperture 144, as shown best in FIG. 6, and has a recessed end surface 156. Note that the proximal end wall 146 of the tubular gripping tool similarly has a recessed surface 148 facing the recessed end surface 156 of the rod.

FIG. 7 depicts the assembly of FIG. 6 in association with a manually operated plier-like force-generating device 170, the device having handles 172, oppositely facing nose portions 174 receivable in the aperture in the gripping tool, and a pivot 176 positioned to provide substantial mechanical advantage to the nose portions. Nose portions 174 bear against the respective recessed surfaces of the push rod and gripping tool as shown in FIG. 7; squeezing of the handles together results in the application of substantial force to the rod 150, causing the clamp 130 to elongate slightly but sufficiently to enable the clamp to be inserted in the bore of the stem. A tooth and pawl mechanism 178 of known design and commonly used with surgical instruments is provided at the ends of the handles to hold them together and thus maintain the stem in its stressed, elongated configuration. Various other devices capable of delivering substantial force to stretch the clamp may be employed using any of a number of mechanical, pneumatic, and hydraulic means.

In use, referring again to FIGS. 4 through 7, a push rod 150 is inserted in an appropriate clamp 130, and the proximal end of the clamp is screwed onto the end of the gripping tool 140 to form the assembly shown in FIG. 6. The nose portions 174 of the force-generating device 170 are inserted through the aperture 144 into contact with the respective recessed surfaces of the push rod and gripping tool, and the handles are squeezed toward each other and locked by the mechanism 178, thus holding the clamp in its elongated configuration. Body 120 is received over the stem, and is positioned where desired along the stem by the surgeon during the implantation procedure. Once the stem and body have been properly oriented with respect to each other, and the body has been suitably impacted by the surgeon into the intramedullary canal, the clamp is inserted into the stem bore. Mechanism 178 is then released, resulting in the release of pressure of the nose elements against the push rod and gripping tool. As the clamp 130 expands toward its rest configuration, it bears with substantial force against the walls of the stem, forcing these walls into tight contact with the walls of the bore formed in the body. The gripping tool, of course, is then removed, and the open proximal end of the clamp is capped appropriately if desired.

It may be particularly valuable to utilize the stem of the prosthesis of FIG. 1 itself as the clamp, eliminating the clamp 30. Here, the proximal end of the stem may be internally threaded to receive the distal threaded end of an externally threaded gripping tool similar to that shown at 140 in FIG. 6. The gripping tool and push rod may be longer than that shown in the drawing to allow placement of the neck and body over the gripping tool prior to threading the gripping tool onto the threaded end of the stem.

By appropriately configuring the gripping tool 140, one may loosely position the neck 20 and body 16 on the gripping tool prior to use of the device to elongate the proximal portion of the stem. The push rod 150 is placed in the bore of the stem, and the gripping tool is threaded onto the stem. Once the stem 12 has been elongated by operation of the force generating device and appropriately positioned in the femoral cavity, the neck and body may be brought down over the nose portions and around the stem and positioned as desired within the intramedullary canal.

Desirably, the various parts of the prostheses of the invention that are clamped together are made of metal such as stainless steel, cobalt chrome alloys, titanium alloys or the like as are commonly employed for prostheses manufacture. The clamp, similarly, may be made of a shape memory alloy or of any metal that exhibits an initial proportional relationship between stress and strain (in the range of validity of Hooke's law). Various metals and metal alloys satisfy this requirement, including stainless steel. The ratio of the lateral or transverse strain to the longitudinal or axial strain, commonly referred to as Poisson's ratio, can range from 0.2 to 0.5, depending on the material and its condition. Poisson's ratio for stainless steel, for example, is about 0.28.

The clamps according to the invention preferably are made of a shape memory alloy such as nitinol. Nitinol exhibits a Poisson's ratio of about 0.3, but this ratio significantly increases up to approximately 0.5 or more when the shape memory alloy is stretched beyond its initial elastic limit; that is, when the formation of stress-induced martensite begins to occur. Nitinol is a pseudoelastic material, that is, a material that exhibits superelasticity at room temperature. A number of shape memory alloys are known to exhibit the superelastic/pseudoelastic recovery characteristic, and these are generally characterized by their ability, at room or body temperature, to be deformed from an austenitic crystal structure to a stressed-induced martensitic structure, returning to the austenitic state when the stress is removed. The alternate crystal structures give the alloy superelastic or pseudoelastic properties.

Nitinol clamps of the type referred to above in connection with FIGS. 1 and 3 can readily be elongated up to 8% or more through the use of instruments such as that shown in FIG. 4. Using nitinol with an assumed Poisson's ratio of 0.3, if a clamp such as that shown in FIG. 6 is elongated 8%, it would be expected to shrink about 2.4% in diameter. If the initial diameter of a clamp were in the neighborhood of ½ inch, the decrease in diameter would be on the order of 0.012 inches. Since tooling tolerances for the internal bores of stems and other prosthesis parts can easily be held within ±0.002 inches, a change of 0.012 inches in the clamp diameter allows substantial room for design variations in size. It is generally preferred that the diameter of the stem bore, however, be only very slightly greater than the outer diameter of the clamp when the clamp is longitudinally stretched to an elongation of, for example, 8%.

A surgeon may select the desired sizes of the stem, body and head, and can assemble the same during a surgical procedure. With reference to the femoral implant shown in FIG. 4, an articulating ball 124 of the appropriate size is selected and is mounted as described above to the neck 120. The femoral prosthesis without the clamp 130 is then assembled. Assembly may take place away from the patient if the desired dimensions and respective angles of the prosthesis parts are known with accuracy ahead of time, as by measurement or by use of trial prosthesis parts. The prosthesis itself can be assembled in the intramedullary canal of the patient, with the correct orientations of the parts noted. Referring to FIGS. 4 through 7, once the parts have been arranged and oriented as desired in the intramedullary canal, a clamp 130 is tensioned to reduce its diameter through use of the gripping tool 140, the pushrod 150 and the force generating device 170, and is then gently placed in the bore of the stem. When tension on the clamp is withdrawn, the clamp expands immediately toward its larger diameter "rest" configuration, thereby clamping itself to the stem and clamping the stem 112 to the body 120. It will be noted that the resulting prosthesis desirably has no threaded fastenings to come loose. While tension is maintained on the clamp, the body 120 may be positioned independently in axial and rotational directions on the stem as the surgeon may deem appropriate for the particular patient. In the same manner in which assembly was carried out, disassembly can be afforded by reversing the steps.

Similarly in connection with the prosthesis of FIG. 3, once the shoulder 78 and stem 72 have been mounted in the distal end of the tibia as desired and oriented with respect to one another, the clamp 80 may be inserted in the bore 82 and permitted to expand toward its "rest" configuration. This, in turn, forces the walls of the stem outwardly and to contact with the bore 84 of the shoulder 78 to lock the stem and shoulder together.

Although the clamp of the invention has been described in terms of a hollow rod with one open end and one closed end, it should be understood that a variety of clamp configurations may be employed. If a change of shape of the clamp due to a martensite to austenite shape memory alloy phase change is desired, then a solid rather than hollow clamp may be preferred. Hollow structures are preferred even in this instance, however, in that the hollow interior of the clamp provides a means for cooling the clamp in the event that a prosthesis needs to be disassembled. Also, while it is desired that the outer surface of the clamp and the inner surfaces of the bore or bores within which the clamp is received be smooth and regular so as to make good surface-to-surface contact, the outer surface of the clamp may, in fact, be ridged or roughened or longitudinally fluted or otherwise configured, as desired.

Moreover, as noted above, the clamps of the invention need not be round in cross section nor must they have a uniform dimension transverse to the longitudinal axis. If desired, the outer surface of the clamp may have a greater transverse dimension in some areas than in others. For example, with reference to FIG. 1, the transverse dimension of the clamp may be greater near the top of the clamp where the stem portion that is clamped bears also against the bore of the body or vice versa.

Figure 8:
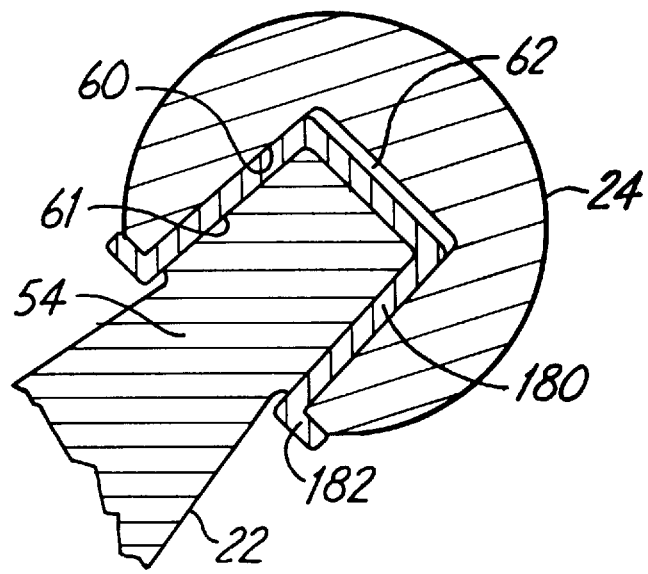
FIG. 8 is a cross-sectional, broken away view showing another embodiment of the invention.

The clamp may in fact be hollow or tubular in design. Referring to FIG. 8, head 54 of the neck extension 22 may be formed with a thimble-shaped clamp 180 having an outwardly flared skirt 182 at its open end. When the head 54 with clamp 180 attached is forced into the bore 60 of the ball (leaving a gap 62 between the end of the clamp 180 and the floor of the bore 60), the rim of the opening 60 encounters the skirt 182 and forces the walls of the clamp to elongate. Upon release of the pressure forcing the head 54 into the opening 60, the walls of the clamp increase slightly in thickness, wedging the ball onto the head 54 and sealing the opening 60. The interface 61 between the head 54 and the clamp 180 is also sealed.

In a preferred embodiment, the confronting walls of the clamp and cavity may be so configured that any slippage between the clamp and the cavity results in the clamp being urged more deeply into the cavity. For example, the confronting walls of the clamp or cavity or both may be configured to have circumferential shoulders or tapered surfaces or other shapes, that coact to preferentially urge the clamp to move or "walk" in one direction rather than the opposite direction upon repeated slippage between the confronting surfaces. With reference to FIG. 4, for example, the diameters 131, 133 of the clamp 130 and the bore in the stem 112 may be slightly greater near the distal end of the stem 112 than near the proximal end so that any movement or "walking" of the clamp due to repeated slippage of the clamp and the stem bore urges the clamp distally within the stem, drawing the widened threaded shoulder at the proximal end of the clamp into contact with the proximal end 126 of the stem.

While a preferred embodiment of the present invention has been described, it should be understood that various changes, adaptations and modifications may be made without departing from the spirit of the invention and the scope of the appended claims.

What is claimed is:

1. A kit for making a modular prosthesis comprising a first prosthesis member having walls defining a cavity having an internal surface, and a clamp comprising a metal rod having an axis and an external surface, the rod having a first, rest configuration having a predetermined dimension in a direction transverse to its axial direction and being configured to accommodate an external stretching force applied thereto during insertion of said rod at least partially into said cavity, said rod being responsive to said external stretching force to assume a second shape having a lesser dimension in said transverse direction with concurrent increase in its axial length to permit the rod to be at least partially inserted into said cavity, said predetermined transverse dimension being such that upon withdrawal of the external stretching force, the clamp returns toward its rest configuration with consequent increase in its dimension in said transverse direction sufficient to bring said internal surface of the cavity and the external surface of the rod into surface-to-surface contact to strongly clamp said clamp to said member.

2. A kit for making a modular prosthesis comprising a first member having walls defining a cavity having an internal surface, a second member having a cavity with an inner surface configured to snugly receive and confront a surface of at least a portion of the first member, and a clamp comprising a metal rod having superelastic properties at body temperature, the rod having an axis and an external surface, the rod having a first, rest configuration having a predetermined dimension in a direction transverse to its axis direction and being configured to accommodate an external stretching force applied thereto during insertion of said rod at least partially into said cavity of said first member, said rod being responsive to said external stretching force to assume a second shape having a lesser dimension in said transverse direction with concurrent increase in its axial length to permit the rod to be at least partially inserted into the cavity of the first member, said predetermined transverse dimension being such that upon withdrawal of the external stretching force, the rod returns toward its rest configuration with consequent increase in its dimension in the transverse direction sufficient to bring said internal surface of the cavity of the first member and the external surface of the rod into surface-to-surface contact and to bring said confronting surfaces of the first and second members into surface-to-surface contact to strongly clamp said members together.

3. A kit for a modular prosthesis comprising a first prosthesis member having walls defining a cavity and a clamp releasably clampable within said cavity, the clamp having superelastic properties at body temperature and having a first, rest configuration having a predetermined dimension in one direction, an instrument configured to apply, during insertion of said clamp into said cavity, a stretching force to said clamp in a second direction normal to said one direction to reduce said dimension in the one direction enough to permit said clamp to be inserted into said cavity, said predetermined dimension being such that upon removal of the stretching force, the clamp returns toward its rest configuration with consequent increase in its dimension in the one direction sufficient to strongly clamp to said member.

4. The kit of claim 3 wherein said clamp comprises a rod having end portions and said instrument includes means for releasably gripping the rod adjacent one of its end portions and means for imparting axial tensile force to the other end portion of the rod to stretch the rod.

5. The kit of claim 3 wherein said clamp comprises a rod having end portions and wherein said instrument comprises a handle including a manual squeezing element, means for releasably gripping the rod adjacent one of its end portions and means responsive to squeezing of the handle to impart axial tensile force to the other end portion of the rod to stretch the rod.

6. The kit of claim 5 wherein said rod has an axial bore open at one end and a fastener adjacent said open end, and wherein said releasable gripping means includes means for fastening to said fastener.

7. The kit of claim 6 wherein said instrument includes a shaft receivable through the open end of the bore and engaging the rod adjacent its other end portion for imparting tensile axial force to the rod.

8. The kit of claim 3 wherein said clamp is hollow and has an inner surface.

9. The kit of claim 8 including a second prosthesis member having a portion received within said hollow clamp, said clamp clamping together said first and second prosthesis members.

10. The kit of any one of claims 1, 2 and 3 wherein said first member comprises an elongated stem receivable in the marrow cavity of a long bone, the stem having an axial bore forming first member said first member cavity.

11. The kit of any of claims 1, 2 and 3 wherein confronting walls of the clamp and cavity are so configured as to urge the clamp toward one direction rather than the opposite direction with respect to the cavity upon any repeated slippage between said confronting walls.

12. The kit of any of claims 1, 2 and 3 wherein the clamp and cavity have confronting walls that are tapered outwardly from a first position to a second position along the cavity so that any slippage between confronting surfaces of the clamp and cavity tends to draw said clamp toward said second position.

13. The kit of any of claims 1, 2 and 3 wherein the clamp and cavity have confronting surfaces so configured as to resist movement between the clamp and cavity due to repeated slippage of either of the confronting surfaces with respect to the other.

14. A kit for making a modular prosthesis comprising a first member having walls defining a cavity and a clamp releasably clampable within said cavity and comprising a metal rod having an axial bore closed at one end, the rod having an axial dimension and a transverse dimension that is increased upon decrease in said axial dimension and wherein said cavity is shaped to axially receive said rod, the rod having a first, rest position having a predetermined dimension in a transverse direction preventing its reception in said cavity, and being capable, upon application of physical stress, of assuming a second shape having a lesser dimension in said transverse direction with concurrent increase of a dimension in an axial direction to permit said rod to be at least partially received in said cavity, said predetermined dimension being such that upon release of said applied physical stress, the rod returns toward its rest configuration with consequent increase in its dimension in the transverse direction sufficient to strongly clamp to said member.

15. The kit of claim 14 wherein said cavity has a surface that is congruent to a surface of the clamp that is received in the cavity to provide surface-to-surface contact of the clamp to the cavity.

16. The kit of claim 14 wherein said prosthesis includes a second member configured to snugly receive at least a portion of the first member in any of several orientations, and wherein said cavity walls are configured to expand into clamping contact with said second member as said clamp moves from its second shape toward its first shape to fixedly support the second member in a predetermined orientation with respect to the first member.

17. The kit of claim 14 including instrumentation for clamping said rod to said first member, the instrumentation including means insertable in said bore for bearing against said closed bore end to elongate the rod sufficiently to enable it to be received in the cavity.

18. The kit of claim 17 wherein said instrumentation includes a handle including a manual squeezing element, means for releasably gripping the rod adjacent an end thereof, and means responsive to squeezing of the handle to impart axial tensile force to the other end of the rod to stretch the rod.

19. A kit for a modular prosthesis comprising a first prosthesis member having walls defining a cavity, a clamp releasably clampable within said cavity, the clamp having walls defining an exterior surface and a hollow interior, said clamp having superelastic properties at body temperature and having a first, rest configuration having a predetermined wall thickness, and a second prosthesis member having an elongated portion sized for reception within said clamp and configured to apply a stretching force to said clamp upon insertion of said elongated portion into said clamp to reduce the thickness of said clamp walls, said clamp being sized such that upon release of said stretching force, said clamp clamps to said cavity and to said elongated portion of said second prosthesis member as said clamp walls return toward said predetermined wall thickness.

20. The kit of claim 19 wherein said hollow clamp has a closed end and an open end defining an outwardly extending skirt at its open end, the cavity of said first member having a rim sized to encounter and bear against said skirt when said elongated portion of the second member is forced into the hollow interior of the clamp.

* * * * *